United States Patent [19]

Teshirogi

[11] Patent Number: 5,013,840

[45] Date of Patent: May 7, 1991

[54] POLYAMIC ACID OR POLYIMIDE

[75] Inventor: Takuma Teshirogi, Fujisawa, Japan

[73] Assignee: Polyplastics Co., Ltd., Osaka, Japan

[21] Appl. No.: 454,031

[22] Filed: Dec. 20, 1989

Related U.S. Application Data

[62] Division of Ser. No. 261,079, Oct. 21, 1988, Pat. No. 4,910,308.

[30] Foreign Application Priority Data

Oct. 23, 1987 [JP] Japan .................................. 62-267989
Oct. 23, 1987 [JP] Japan .................................. 62-267990

[51] Int. Cl.$^5$ .......................................... C07D 241/02
[52] U.S. Cl. ...................................... 544;357; 544/336; 544/405
[58] Field of Search ........................ 544/405, 336, 357

[56] References Cited

PUBLICATIONS

March, Advanced Organic Chemistry, 3rd Edition; p. 371, reaction 0–55, Acylation of Amines by Anhydrides.

Primary Examiner—Cecilia Shen
Attorney, Agent, or Firm—Birch, Stewart, Kolasch & Birch

[57] ABSTRACT

A polyamic acid or polyimide having 2,5-distyrylpyrazine units in the main chain thereof.

3 Claims, 4 Drawing Sheets

POLYAMIC ACID OR POLYIMIDE

This application is a divisional of application Ser. No. 07/261,079 filed on Oct. 21, 1988, now U.S. Pat. No. 4,910,308.

The present invention relates to a novel diolefinic compound having a substituent at the 4-position of 2,5-distyrylpyrazine and a process for its preparation.

The present invention relates to a novel linear polyamic acid or linear polyimide having 2,5-distyrylprazine units in its main chain and a process for preparing the same.

STATEMENT OF PRIOR ARTS

Diolefinic compounds, such as 2,5-distyrylpyrazine having a rigid molecular structure, are known to undergo solid-state polymerization to give a highly crystalline polymer with a high molecular weight. But no compound having an amino group at the 4-position of a phenyl ring of 2,5-distyrylpyrazine has ever been disclosed.

An aromatic polyimide has excellent mechanical, electrical, physical, and chemical properties and is widely used for electronics, electric field, precision instruments, etc., in the form of a film, varnish, and molded article. A linear aromatic polyimide has hiterto been synthesized by allowing an aromatic tetracarboxylic dianhydride, such as pyromellitic dianhydride, benzophenonetetracarboxylic anhydride or diphenyl ether tetracarboxylic dianhydride, to act on an aromatic diamine, such as phenylenediamine, diaminodiphenyl, diaminodiphenylmethane, diaminodiphenyl ketone, diaminodiphenyl ether, diaminodiphenyl thioether or diaminodiphenyl sulfone, to prepare a polyamic acid and then subjecting the polyamic acid to thermal ring closure.

However, the aromatic polyamic acid and aromatic polyimide comprising 2,5-bis(4-aminostyryl)pyrazine as an aromatic diamine component according to the present invention, namely, a polyamic acid and a polyimide having a rigid molecular skeleton and containing 2,5-distyrylpyrazine units having high photoreactivity in its polymer main chain have not been known.

SUMMARY OF THE INVENTION

The present inventor has made extensive and intensive studies of a 2,5-distyrylpyrazine compound having an amino group at the 4-position thereof and, as a result, have synthesized a novel compound, i.e., 2,5-bis(4-acetaminostyryl)pyrazine and 2,5-bis(4-aminostyryl)-pyrazine, which has led to the completion of the present invention.

Specifically, the present invention provides a 2,5-distyrylpyrazine compound represented by following structural formula (I)

wherein X is COCH$_3$ or H, i.e., 2,5-bis(4-acetaminostyryl)pyrazine and 2,5-bis(4-aminostyryl)pyrazine respectively represented by following structural formulae (IV) and (V):

The compound of the present invention can be prepared via the following synthetic pathway. Specifically, 2,5-bis(4-acetaminostyryl)pyrazine (IV) can be prepared by allowing p-acetaminobenzaldehyde to act on 2,5-dimethylpyrazine in the presence of a condensing agent. 2,5-bis(4-aminostyryl)pyrazine (V) can be prepared by deacetylation of 2,5-bis(4-acetaminostyryl)-pyrazine under acidic conditions.

(IV)

↓ B (V)

In above-described formula (1), letter A designates a condensing agent comprising polyphosphoric acid, acetic anhydride, sulfuric acid, benzoic anhydride, zinc chloride, or a mixture thereof. However, the condensing agent is not limited to these only, and any compound having a condensation activity can be used. Letter B designates an acid catalyst such as hydrochloric, sulfuric, p-toluenesulfonic, or phosphoric acid. However, the acid catalyst is not limited to these only, any Brønsted acid can be used.

The compound of the present invention is a bifunctional monomer having a highly reactive amino group and therefore is useful for all classes of polymers prepared from a starting monomer comprising a diamine component. For example, the compound of the present invention is useful as a monomer for polyamide, polyimide, polysulfonamide, polyurea, polyamine, etc., i.e., a polymer having an amide, imide, sulfonamide, urea or amino bond and a polymer having a combination of these bonds.

Further, the compound of the present invention forms an adduct having a cyclobutane ring through [2+2] photocycloaddition. Moreover, the compound of the present invention has such a property that the cyclobutane ring or pyrazine ring is photocleaved upon being exposed to short-wavelength light.

Therefore, the compound of the present invention is useful as a photoreaction reagent or an optical recording material which utilize the above-described properties. Since the compound of the present invention per se is a fluorescent substance, it is suitable also for use as a brightener and an analytical or measuring reagent as a photoreactive fluorescent substance.

The present inventor has made extensive and intensive studies on an aromatic polyamino acid and an aromatic polyimide having a rigid molecular structure and then photoreactivity and comprising 2,5-bis(4-aminostyryl)pyrazine as a diamine component and, as a result, have accomplished the invention of the present application.

Specifically, the present invention provides a polymer represented by following general formula [XI] more particularly an aromatic polyamic acid represented by following general formula [XIV] and an aromatic polyimide represented by following general formula [XV]:

[XI]

wherein X is

Ar is an aromatic tetrafunctional residue and n is an integer of 2 or more:

[XIV]

and

The polymer of the present invention can be prepared via the following synthetic pathway.

Specifically, 2,5-bis(4-aminostyryl)pyrazine represented by formula [XII] is reacted with a tetracarboxylic dianhydride represented by following general formula [XIII] to prepare a polyamic acid of formula [XIV].

2,5-Bis(4-aminostyryl)pyrazine can be prepared via the following synthetic pathway. Specifically, p-acetaminobenzaldehyde (b) is allowed to act on 2,5-dimethylpyrazine (a) in the presence of a condensing agent to prepare 2,5-bis(4-acetaminostyryl)pyrazine (c). The 2,5-bis(4-acetaminostyryl)pyrazine can be deacetylated under acidic conditions to prepare 2,5-bis(4-aminostyryl)pyrazine [XII].

In above-described reaction formula (1), letter A designates a condensing agent comprising polyphosphoric acid, acetic anhydride, sulfuric acid, benzoic anhydride, zinc chloride, or a mixture thereof. However, the condensing agent is not limited to these only, and any compound exhibiting a condensation activity can be used. Letter B designates an acid catalyst such as hydrochloric, sulfuric, p-toluenesulfonic or phosphoric acid. However, the acid catalyst is not limited to these only, and any Bronsted acid can be used. Then a polyamic acid of formula [XIV] is subjected to thermal ring closure to prepare a polyimide of formula [XV].

The synthesis of a polyamic acid and a polyimide through a reaction of 2,5-bis(4-aminostyryl)pyrazine

[XIV]

[XV]

with a tetracarboxylic dianhydride represented by above-described reaction formula (2) can be conducted under the same conditions as those of the synthesis of usual polyamides. Specifically, a polymer in a film form can be prepared as follows. 2,5-Bis(4-aminostyryl)pyrazine is dissolved in a polar solvent, e.g., dimethylacetamide (DMAc), and a tetracarboxylic dianhydride in a molar amount equal to that of this diamine is added thereto mixing to prepare a polyamic acid solution. This solution is cast and vacuum dried to prepare a polyamic acid film. This film is heat treated for thermal ring closure, thereby preparing a polyimide film.

In the process of the present invention, the aromatic tetracarboxylic dianhydride for use as a starting material in the synthesis of a polyamic acid and a polyimide may be those usually employed in the synthesis of an aromatic polyimide. Especially the aromatic tetracarboxylic dianhydride may be one represented by above described general formula (XIII) wherein Ar is a member selected from the following aromatic tetrafunctional residues. Further the aromatic tetracarboxylic dianhydride may be a mixture of two or more of these dianhydrides.

and

Preferred examples of the tetracarboxylic dianhydride include pyromellitic dianhydride, 2,3,6,7-naphthalene tetracarboxylic dianhydride, 1,4,5,8-naphthalene tetracarboxylic dianhydride, 3,3',4,4'-diphenyltetracarboxylic dianhydride, 3,3',4,4'-benzophenonetetracarboxylic dianhydride, and 3,3',4,4'-diphenyl ether tetracarboxylic dianhydride.

Although the degree of polymerization of the polyamic acid and polyimide according to the present invention is not well-defined, the value of n in above-described general formulae [XIV] and [XV] determined from the value of the reduced viscosity of a solution of the polyamic acid is 50 or more.

The polyamic acid and polyimide according to the present invention are each a polymer having resistance to heat and usual organic solvents comparable to various conventional aromatic polyamic acids and aromatic polyimides. Interestingly, the polyimide of the present invention is soluble in sulfuric acid in which common aromatic polyimides are insoluble, because it has a pyrazine residue in its main polymer chain.

The polyamic acid and polyimide prepared according to the present invention can be utilized as a coating material, film, molding resin, laminate, and composite material. Further, the polyamic acid and polyimide according to the present invention are each a polymer having a high modulus of elasticity because they each have a 2,5-distyrylpyrazine unit comprising a rigid molecular skeleton in its main chain. Moreover, since the polyamic acid and polyimide according to the present invention each have photoreactive double bonds in its main chain, exposure to light brings about [2+2] cycloaddition (said photoreaction bringing about the formation of a three-dimensional structure and the cleavage of the conjugated system). Therefore, the polyamic acid and polyimide according to the present invention can be used for an isotropic polyimide having a high modulus of elasticity, a photosensitive polymer, an optical display material, an optical recording material, or the like by taking advantage of this photoreactivity.

Further, the polyamic acid and polyimide according to the present invention have a pyrazine residue in its main chain. This pyrazine residue imparts a number of interesting characteristics to the polymer. That is, the pyrazine residue is a hydrophilic and basic functional group and can be easily protonated and quaternized.

Therefore, the polyamic acid and polyimide according to the present invention can be applied to a separative membrane, a chelating resin, and an ion exchange resin by taking advantage of the hydrophilic and basic properties of the pyrazine residue. Further, it is possible to use the polyamic acid and polyimide according to the present invention as analytical and measuring reagents.

EXAMPLES

The present invention will now be described in more detail with reference to the following Examples which should not be construed as limiting the scope of the present invention.

EXAMPLE 1

Synthesis of 2,5-bis(4-acetaminostyryl)pyrazine 10.8 g (0.1 mol) of 2,5-dimethylpyrazine, 36.0 g (0.2×1.1 mol) of p-acetaminobenzaldehyde, and 1.0 g of $ZnCl_2$ were placed in a round-bottomed flask, and allowed to react on an oil bath at 180° C. for 4 hr and then at 200° C. for 2 hr. 200 ml of dimethylacetamide (DMAc) was added to the reaction mixture, followed by reflux for 10 min. The reaction mixture was transferred to an Erlenmeyer flask through a filter paper. The same procedures were repeated by making use of 200 ml of DMAc and finally 100 ml of DMAc. The crystals thus precipitated were collected by filtration and recrystallized from DMAc.

Amount of product: 23.6 g.
Yield: 59.3%.

| Results of elementary analysis | | | | | |
|---|---|---|---|---|---|
| C (%) | | H (%) | | N (%) | |
| calculated | found | calculated | found | calculated | found |
| 72.34 | 72.59 | 5.57 | 5.48 | 14.06 | 14.06 |

Figure 1:
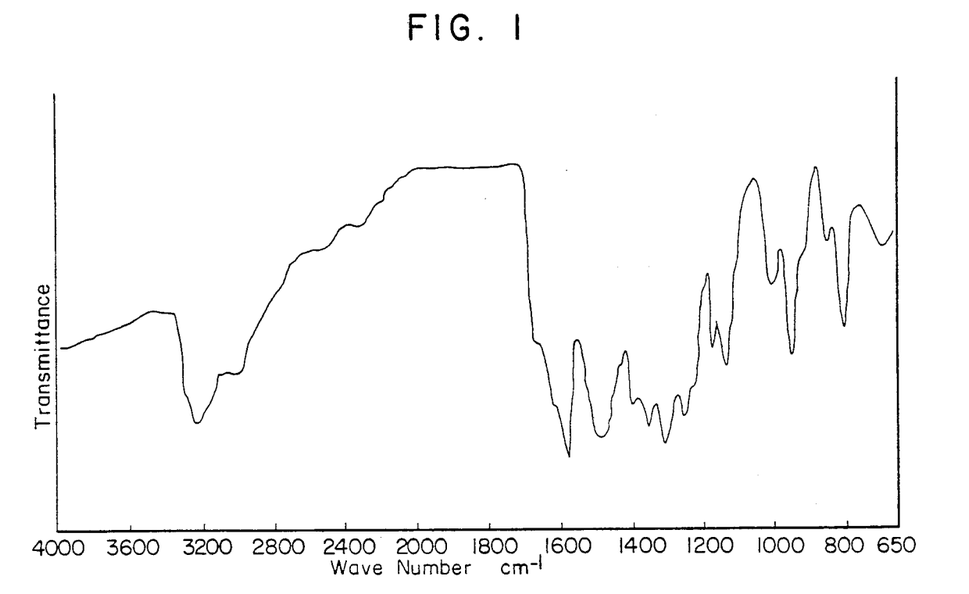
FIGS. 1 and 2 are respectively charts of an infrared absorption spectrum and a 300 MHz $^1$H-NMR spectrum of 2,5-bis(4-acetaminostyryl)pyrazine prepared in Example 1.
Figure 2:
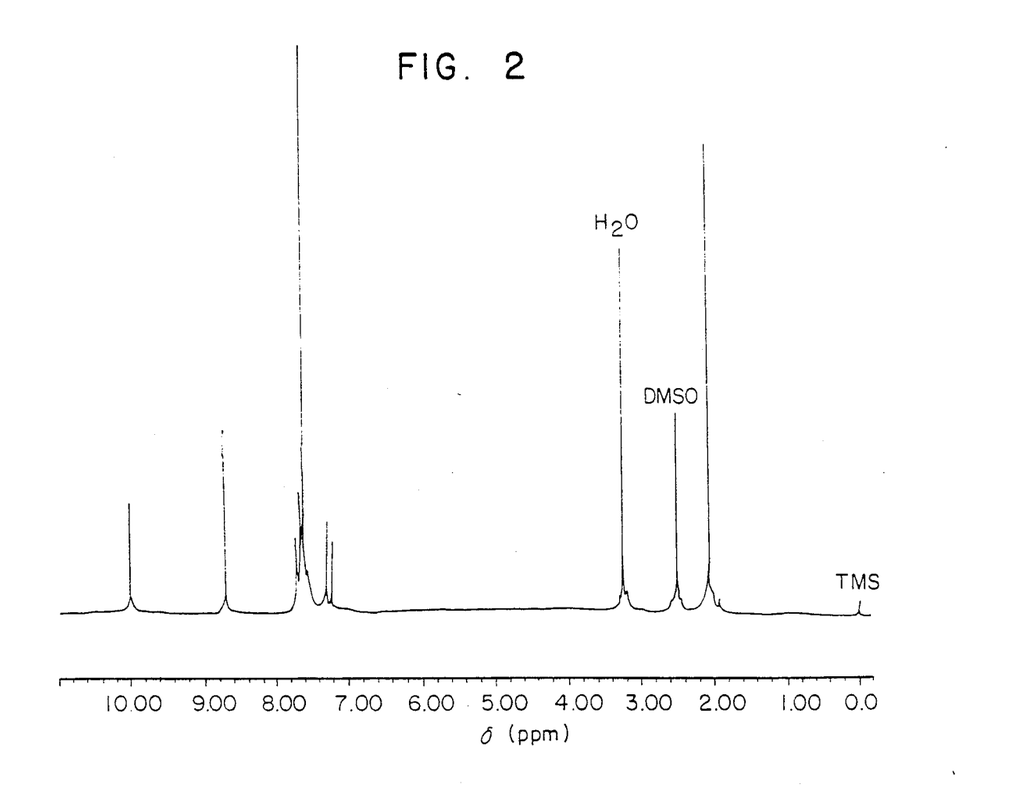

An infrared absorption spectrum (KBr disk method) and a 300 MHz $^1$H-NMR spectrum [solvent: dimethyl sulfoxide-$d_6$ (DMSO-$d_6$), internal reference: tetramethylsilane (TMS)] 2,5-bis(4-acetaminostyryl)pyrazine are shown in FIGS. 1 and 2, respectively.

IR (KBr disk method): 3307, 1664, 1592, 1535, 1411, 1367, 1321, 1268, 973, 823 cm$^{-1}$.

H-NMR (300 MHz; DMSO-$d_6$): δ2.07(s, 6H), δ7.2–7.3(d, 2H), δ7.5–7.8(m, 10H), δ8.70(s, 2H), δ9.99(s, 2H) ppm.

EXAMPLE 2

Synthesis of 2,5-bis(4-aminostyryl)pyrazine 10.0 g of 2,5-bis(4-acetaminostyryl)pyrazine prepared in Example 1 was refluxed together with 100 ml of concentrated hydrochloric acid for 6 hr. The reaction mixture was allowed to cool and filtered. The collected product was dispersed in 200 ml of water and then alkalinized to a strongly alkaline state with sodium hydroxide. The product was collected by filtration, recrystallized from DMAc containing a small amount of water, and recrystallized from DMAc.

Amount of product: 5.6 g.
Yield: 71.0%.

| Results of elementary analysis | | | | | |
|---|---|---|---|---|---|
| C (%) | | H (%) | | N (%) | |
| calculated | found | calculated | found | calculated | found |
| 76.41 | 76.38 | 5.77 | 5.63 | 17.82 | 17.62 |

Figure 3:
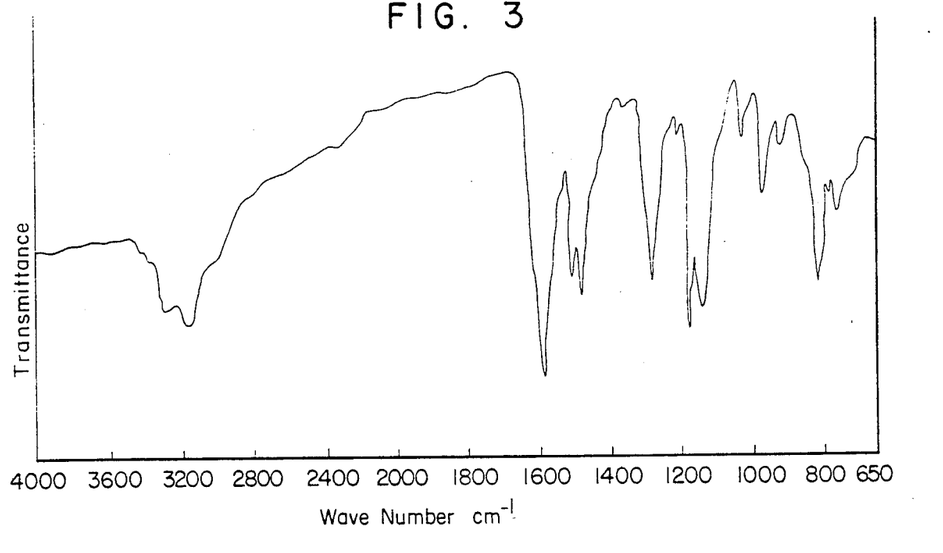
FIGS. 3 and 4 are respectively charts of an infrared absorption spectrum and a 300 MHz $^1$H-NMR spectrum of 2,5-bis(4-aminostyryl)pyrazine prepared in Example 2.
Figure 4:
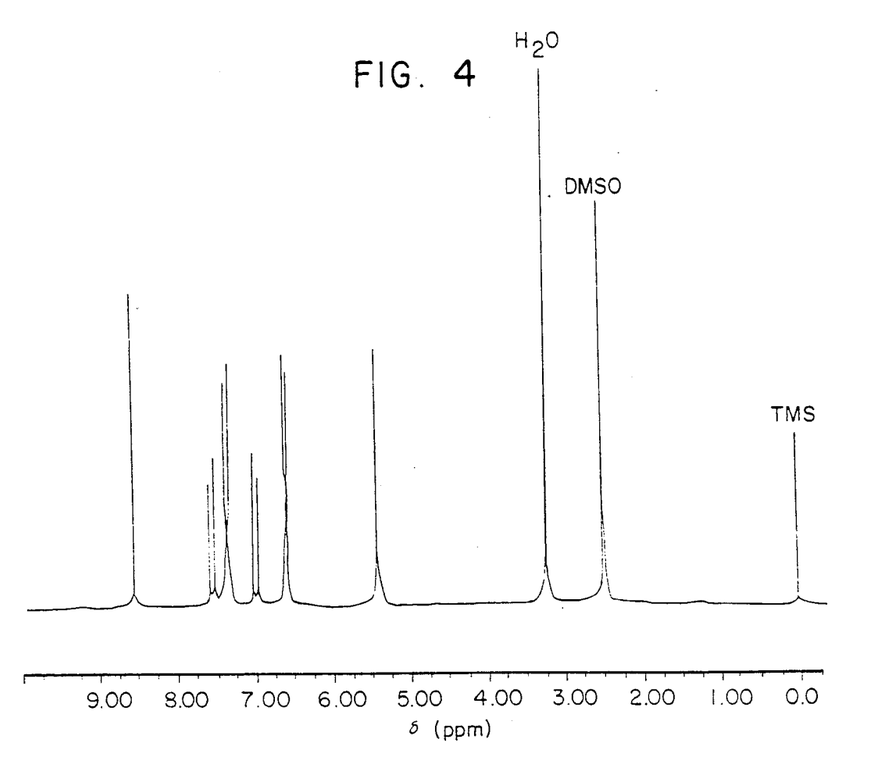

An infrared absorption spectrum (KBr disk method) and a 300 MHz $^1$H-NMR spectrum [solvent: DMSO-$d_6$, internal reference: TMS] of 2,5-bis(4-aminostyryl)pyrazine are shown in FIGS. 3 and 4, respectively.

IR (KBr disk method): 3318, 3197, 1596, 1515, 1483, 1286, 1178, 1151, 1027, 975, 817 cm$^{-1}$.

$^1$H-NMR (300 MHz; DMSO-$d_6$): $\delta$5.42(s, 4H), $\delta$6.5–6.7(d, 4H), $\delta$6.9–7.1(d, 2H), $\delta$7.3–7.5(d, 4H), $\delta$7.5–7.7(d, 2H), $\delta$8.54(s, 2H) ppm.

EXAMPLE 3

Evaluation of Photoreactivity

The photoreactivity of crystalline 2,5-bis(4-acetoaminostyryl)pyrazine and 2,5-bis(4-aminostyryl)pyrazine prepared in Examples 1 and 2 was examined. The photoreactivity was evaluated by exposure to light from a 100-W high-pressure mercury lamp at room temperature for 24 hr. In the IR spectrum, there was observed a decrease in the absorption peak assignable to an olefin, suggesting the occurrence of a photoreaction. Further, these compounds showed fluorescence having a bluish purple color and brought about a reaction upon being exposed to light in solution. The reaction was confirmed by the thin layer chromatography.

EXAMPLE 4

0.314 g (0.001 mol) of 2,5-bis(4-aminostyryl)pyrazine was placed in an Erlenmeyer flask equipped with a cap and containing a stirring bar to disperse it in 4.0 ml of DMAc. Then, 0.332 g (0.001 mol) of powdery pyromellitic dianhydride (PMDA) was added thereto in portions. The mixture was stirred at room temperature for 12 hr. The resultant viscous polyamic acid solution was sampled to measure the reduced viscosity in a concentration of 0.2 g/dl. Since the polyamic acid has a high viscosity, 4.0 ml of DMAc was further added thereto and the mixture was stirred. The resultant solution was cast on an aluminum foil, heated and dried at 80° to 100° C. in vacuo, thereby preparing a polyamic acid film. The polyamic acid on the aluminum foil was dried and dehydrated at 220° C. for 10 hr in vacuo, and then cooled. The cooled aluminum foil was treated with a diluted hydrochloric acid, washed with water and air-dried to recover polyimide film.

Figure 5:
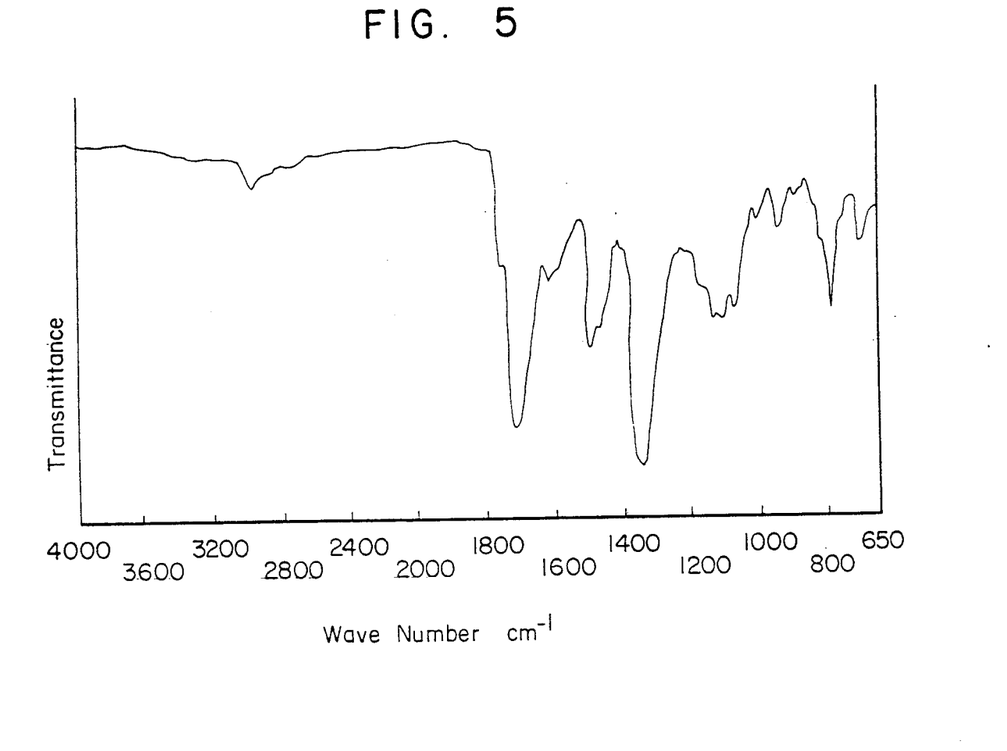
FIGS. 5 and 6 are charts of infrared absorption spectra of aromatic polyimides prepared in Examples 4 and 5, respectively.

An infrared absorption spectrum of this aromatic polyimide is shown in FIG. 5. Supposedly the reaction proceeds as shown in the following reaction formula:

EXAMPLE 5

A polyamic acid and a polyimide film were prepared in the same manner as that of Example 4 except that 3,3′,4,4′-benzophenonetetracarboxylic dianhydride (BTDA) was used as the tetracarboxylic dihydride.

Figure 6:
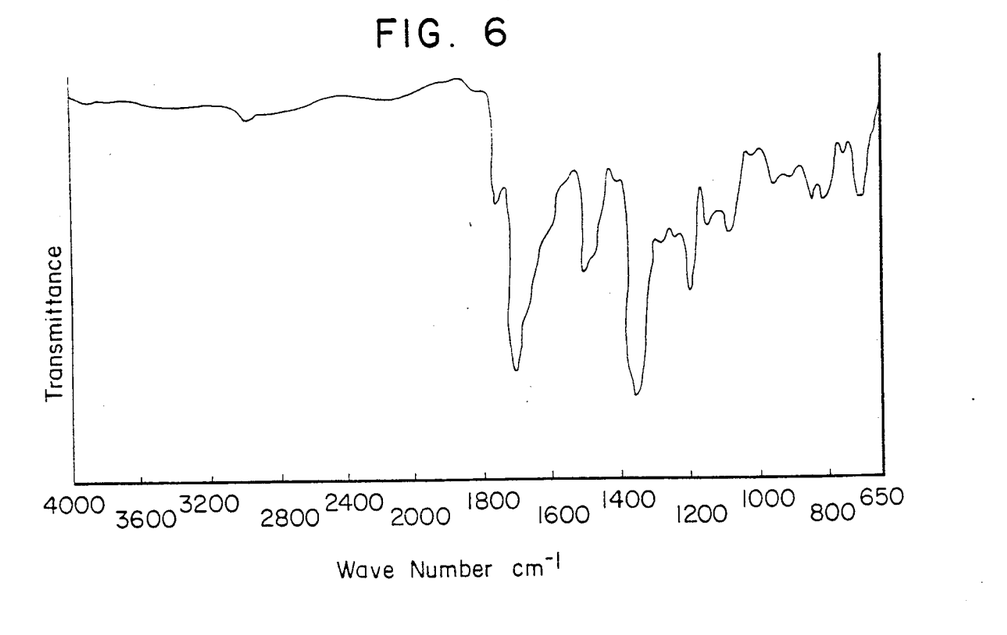

An infrared absorption spectrum of the polyimide thus prepared is shown in FIG. 6. Presumably the reaction proceeds via the same pathway as that of Example 4.

EXAMPLE 6

Heat stability (TGA) of polyimide

Figure 7:
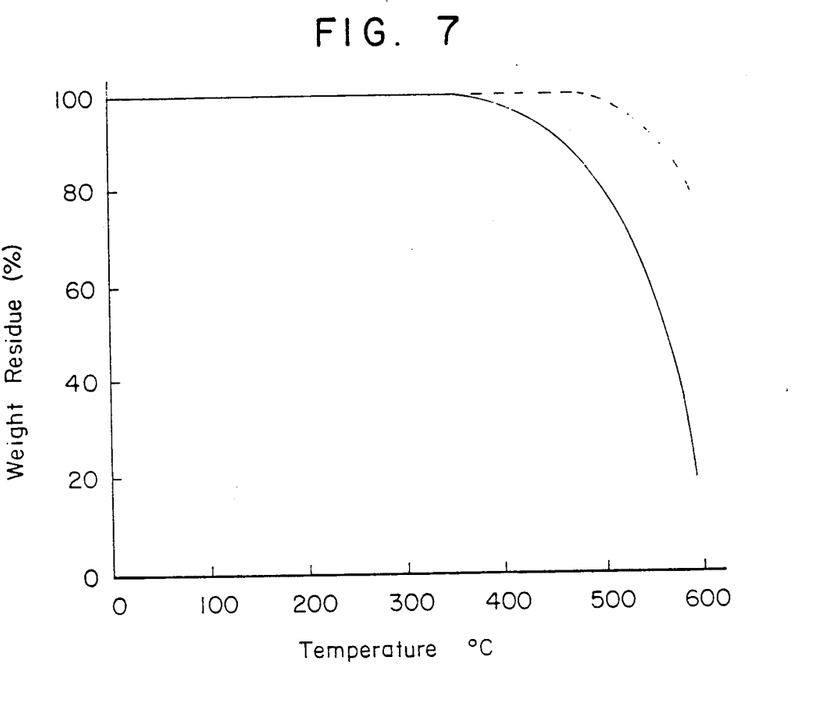
FIGS. 7 and 8 are thermogravimetric curves of aromatic polyimides prepared in Examples 4 and 5, respectively.
Figure 8:
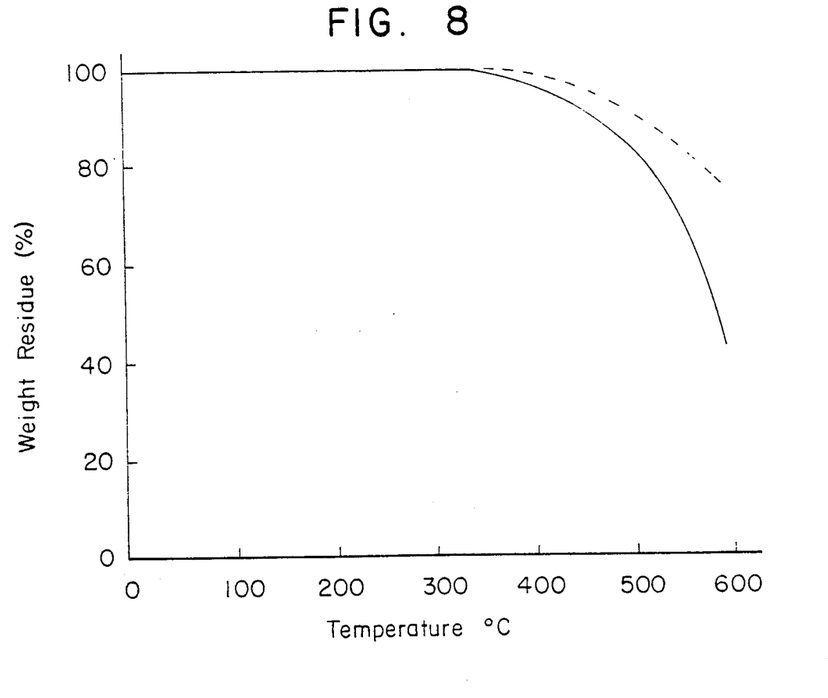

A polyimide film was applied to thermogravimetric analysis, and heat stability thereof was determined from a 10% weight loss temperature and a pyrolysis curve. The TGA curves are shown in FIGS. 7 and 8. The 10% weight loss temperatures in air and in nitrogen are shown in Table 1. FIG. 7 is a TGA curve of a polyimide prepared from PMDA (Example 4), while FIG. 8 is a TGA curve of a polyimide prepared from BTDA (Example 5). In the drawings, a solid line represents the results of measurement in the air, while a dotted line represents the results of measurement in nitrogen.

TABLE 1

|  |  | 10% weight loss temperature (°C.) |
|---|---|---|
| Ex. 4 | air | 456 |
| (PMDA) | $N_2$ | 565 |
| Ex. 5 | air | 465 |
| (BTDA) | $N_2$ | 525 |

EXAMPLE 7

Solubility of polyimide

The solubility of polyimide PMDA and polyimide BTDA respectively prepared from PMDA and BTDA is shown in Table 2.

TABLE 2

| | polyimide | |
|---|---|---|
| solvent | polyimide A PMDA (A) | polyimide B BTDA (B) |
| sulfuric acid | easily soluble | easily soluble |
| hydrochloric acid | swelling | swelling |
| trifluoroacetic acid | swelling | swelling |
| dimethylformamide | insoluble | insoluble |
| m-cresol | insoluble | insoluble |
| hexafluoro-2-propanol | insoluble | insoluble |

The color of the polyimide PMDA turned from reddish purple to deep reddish purple in hydrochloric acid and trifluoroacetic acid. In the same solvents, the color of the polyimide BTDA turned from yellow to deep reddish purple.

EXAMPLE 8

Photoreactivity of polyimide

Polyimide films respectively prepared from PMDA and BTDA were exposed to light from a 500-W high-pressure mercury lamp for 24 hr, which brought about a decrease in an intensity of the infrared absorption peak assignable to an olefin.

I claim:
1. A polyamic acid or a polyimide represented by the following formula [XI]

wherein X is

Ar is an aromatic tetrafunctional residue selected from the group consisting of and a mixture thereof, and n is an integer of 2 to 50.

2. A polyamic acid represented by the following formula [XIV]

[XIV]

[XV]

wherein Ar is an aromatic tetrafunctional residue selected from the group consisting of and a mixture thereof,
and n is an integer of 2 to 50.

3. A polyimide represented by the following formula [XV]

wherein Ar is an aromatic tetrafunctional residue selected from the group consisting of and a mixture thereof,
and n is an integer of 2 to 50.

* * * * *